United States Patent [19]

Papadofrangakis et al.

[11] 4,257,278
[45] Mar. 24, 1981

[54] QUANTITATIVE VOLUME BLOOD FLOW MEASUREMENT BY AN ULTRASOUND IMAGING SYSTEM FEATURING A DOPPLER MODALITY

[75] Inventors: Emmanuel Papadofrangakis, Schenectady, N.Y.; John A. Fakiris, Holly Hill, Fla.

[73] Assignee: General Electric Company, Schenectady, N.Y.

[21] Appl. No.: 69,357

[22] Filed: Aug. 24, 1979

[51] Int. Cl.$^3$ .................................................. G01F 1/66
[52] U.S. Cl. .................................... 73/861.25; 128/663
[58] Field of Search ...................... 73/861.25, 641, 642; 128/663

[56] References Cited

U.S. PATENT DOCUMENTS

| | | | |
|---|---|---|---|
| 3,939,707 | 2/1976 | Kossoff | 73/861.25 |
| 4,062,237 | 12/1977 | Fox | 73/861.25 |
| 4,159,462 | 6/1979 | Rocha et al. | 73/620 X |
| 4,182,173 | 1/1980 | Papadofrangakis et al. | 73/641 |
| 4,217,909 | 8/1980 | Papadofrangakis et al. | 73/861.25 X |

OTHER PUBLICATIONS

C. F. Hottinger et al., "Unambiguous Measurement of Volume Flow Using Ultrasound", *Proceeding of the IEEE*, Jun. 1975.

*Primary Examiner*—Charles A. Ruehl
*Attorney, Agent, or Firm*—Donald R. Campbell; Marvin Snyder; James C. Davis

[57] ABSTRACT

A technique particularly suitable for measuring volume flow rate in the ascending aorta employs real time sector-scan imaging to locate the cross section of interest and align the Doppler beam with the vessel axis. The number of active transmit and receive array transducer elements is varied to electronically tailor the acoustic beam cross section at the required range to be approximately equal to the vessel cross section, which is the sample volume. Mean flow velocity is computed by averaging the spectral components extracted from the sample volume by a Fourier transform processor. Volume flow rate is calculated by multiplying mean flow velocity and estimated area.

6 Claims, 8 Drawing Figures

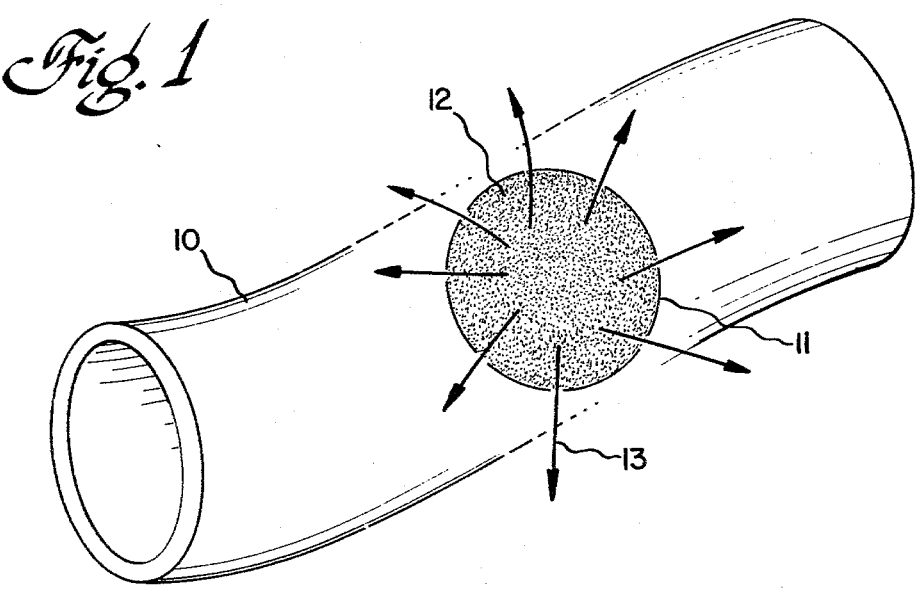
Fig. 1
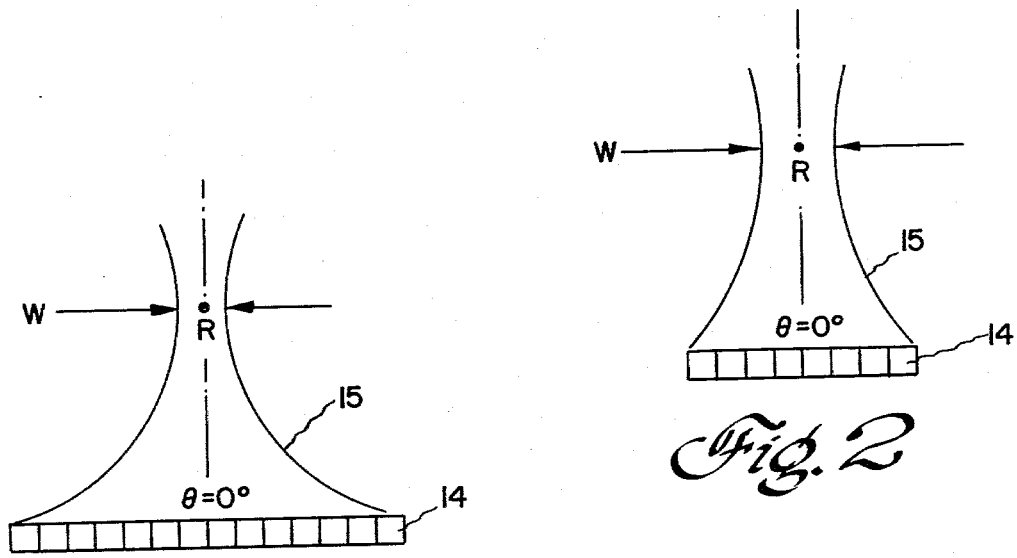
Fig. 2
Fig. 3
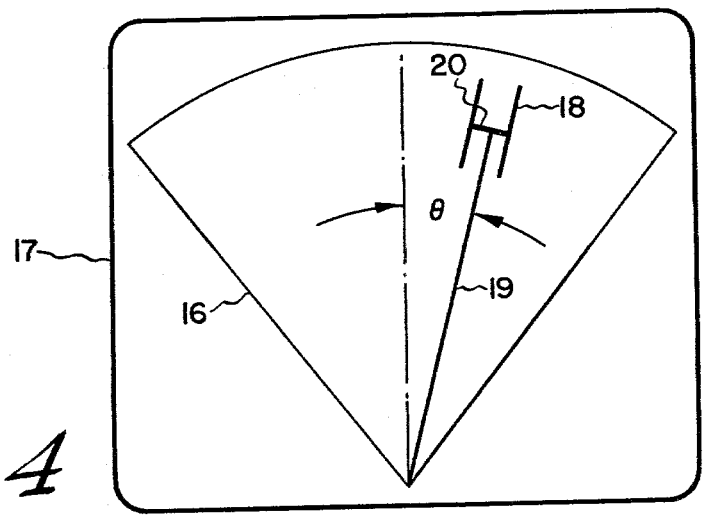
Fig. 4

QUANTITATIVE VOLUME BLOOD FLOW MEASUREMENT BY AN ULTRASOUND IMAGING SYSTEM FEATURING A DOPPLER MODALITY

BACKGROUND OF THE INVENTION

This invention relates to a method for sensing the volume flow rate of blood and similar liquids, and especially to an improved and more convenient measurement technique using a sector scanning steered beam imager having a Doppler mode of operation.

Volume blood flow information is important to the diagnosis of cardiovascular disease. Knowledge of the amount of oxygen being delivered to various regions of the body is a factor that can assist clinicians in the management of disease and trauma. Volume blood flow may be one of the best indicators of available oxygen. It is also an indication of the ability of the heart to function as a pump to maintain normal body processes. In the case of a vessel, volume flow rate is given by the equation $Q = V \cdot A$, where A is the cross-sectional area normal to the vessel center line and V is the velocity of blood passing through the cross-sectional area and at right angles to it. In the circulatory system A and V are not only functions of position, but also of time.

Various methods have been proposed to estimate volume blood flow rate by ultrasound. Most involve making assumptions about the flow conditions and the velocity profile across the vessel lumen. In most, orientation is attempted without imaging help and insonification of the sample volume is performed "blind." Several available flowmeters employ the zero-crossing detection method which gives only a crude estimate of root-mean-square velocity. For narrow Doppler spectra the error in the calculation is not catastrophic. In large vessels such as the abdominal aorta, or in situations involving complex velocity distributions such as at the root of the ascending aorta, the Doppler spectra may be quite broad and the discrepancy unacceptable. An advanced Doppler blood flow instrument is reported by C. F. Hottinger and J. D. Meindl in Proceedings of the IEEE, Vol. 63, No. 6, June 1975, pp. 984,5. This employs a double aperture configuration to illuminate the lumen and estimate its cross-sectional area. It is stated that by electronically forming a ratio of the Doppler signal power returning to the two apertures, orientation ambiguities are removed. U.S. Pat. No. 3,939,707 to G. Kossoff describes the combined use of B-scan imaging and a Doppler technique. The cross-sectional area is determined by measuring the vessel diameter on the display, and the angle between the ultrasonic beam direction for the Doppler measurement and the vessel axis is also estimated and is factored in the velocity reading. This method can lead to errors large enough that the data has little or impaired diagnostic value.

In addition to the problem of correct orientation of the ultrasonic beam with respect to the flow vectors, another difficulty in estimating volume blood flow by transcutaneous ultrasonic transducers arises from the need to define accurately a sample volume which spans the entire vessel cross section. Finally, it is important to process the ultrasound signals echoing from the vessel lumen by a technique that faithfully yields mean velocity readings.

SUMMARY OF THE INVENTION

A sector scan steered beam ultrasound imaging system which has a common transducer array for B-scan imaging and Doppler modalities is first used to obtain on the B-scan display a view of a vessel through which the volume flow rate is to be measured. The system transmits acoustic beams at many angles and one of these is selected that is approximately aligned with the vessel axis, to ensure that in the Doppler mode of operation the direction of the ultrasonic beam and the principal flow vector are colinear. The next task involves establishing a sample volume for the Doppler modality which is approximately the same as the vessel cross section, requiring in most instances a deliberate defocusing of the beam. The number of active array transducer elements for transmit and receive is varied to realize, at a given range, a beam cross section approximately equal to the vessel cross section. The controller generates an area signal representative of the latter cross section. To facilitate system/user interaction there is added to the display subsystem the capability of producing on the display (a cathode ray tube) a beamsteering direction and range marker, and a beam width marker.

To measure the volume flow rate, ultrasonic beams are sequentially generated to insonify the sample volume and received echoes are alternately detected using only the selected active array elements, preferably an equal number of transmit and receive elements. The received echo signals are processed in multiple receiving channels to yield focused in-phase and quadrature signals as taught in U.S. Pat. No. 4,155,260. Pairs of focused signals are range gated after every pulse-echo cycle for a short interval to extract pairs of analog signals representing echoes backscattered from the sample volume, i.e., the chosen vessel cross section. Sets of analog sample pairs are analyzed in a Doppler processor embodying a complex arithmetic implementation of the Fourier transform; this yields the magnitude and sign of the distribution of bidirectional velocities in the sample volume. Mean flow velocity is calculated and the output is multiplied with the area signal to arrive at the volume flow rate. This is done in real time. A strip chart recorder provides a convenient visual display of volume flow rate versus time.

Quantitative blood flow measurement with sufficient accuracy to be of diagnostic value is achieved in the abdominal aorta and the root of the ascending aorta (in an adult the vessel diameter is about one-half inch), these being two of the most important areas of interest to physicians.

BRIEF DESCRIPTION OF THE DRAWINGS

FIG. 1 is a perpective view of a blood vessel showing a sample volume and velocity vectors;

FIGS. 2 and 3 illustrate ultrasound beams having different beam-spot widths and cross sections at a given range;

FIG. 4 is a B-scan image of a large vessel on the screen of a cathode ray tube on which is superimposed a marker for the beamsteering direction and range and a marker for the beam width;

DESCRIPTION OF THE PREFERRED EMBODIMENTS

Figure 5:
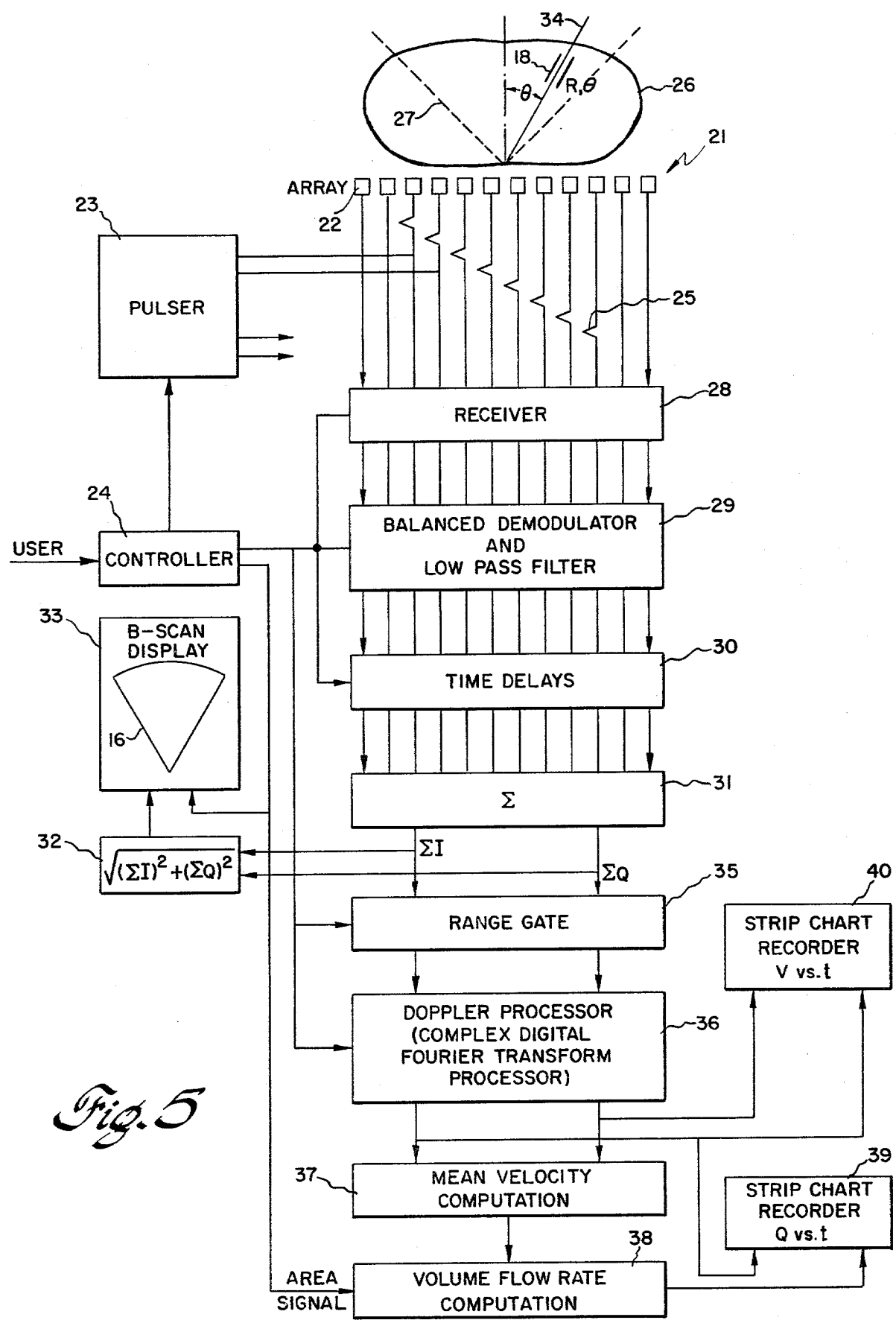
FIG. 5 is a simplified block diagram of a duplex imaging system with a Doppler modality and provision for volume flow rate measurement and display.

The following discussion assumes a knowledge of steered beam or phased array imagers for making wide angle sector scans, and of the duplex ultrasonic imaging system in allowed application Ser. No. 936,115 filed Aug. 23, 1978 by E. Papadofrangakis, J. A.Fakiris, and W. E. Engler, now Pat. No. 4,182,173 the disclosure of which is incorporated herein by reference. This system is reviewed in detail later (FIG. 5) and has a real time single-sector scanner with an incorporated Doppler mode of operation for blood flow velocity measurement capable of improved performance because the same transducer array is used for imaging and velocity measurement. For the latter, the duplex imager has a B-scan imaging and Doppler orientation mode and a Doppler processing and display mode. Doppler orientation involves visual examination of the B-scan image to identify the sample volume through which blood flow velocity is to be determined and to select the beamsteering direction $\theta$ and range R for the Doppler modality. In the Doppler mode of operation the system insonifies the selected direction $\theta$ and is focused at range R, and a Doppler processor reports the ultrasound power spectra backscattered from the sample volume which corresponds to the velocity distribution. The sample volume was chosen to be relatively small (a diameter of approximately 2 mm), and the ultrasonic beam cross section is correspondingly small, because velocity at a specific point can be accurately determined by making the diameter of the sample volume as small as possible.

FIG. 1 shows a large human blood vessel 10 such as an adult aorta with a diameter of about 1.5 cm. For quantitative volume blood flow measurements, the size of sample volume 11 and the ultrasonic beam cross section are made approximately equal to the vessel cross section at the required range. The ultrasonic beam spot-width at this range is electronically tailored by programmable aperture synthesis to cover the whole area of the vessel; the sample volume is shaped. This means deliberately defocusing the ultrasonic beam in order to realize greater accuracy in measuring the volume flow rate. Red blood cells 12 in the blood stream are very small (about 8 microns in diameter) as compared to the ultrasonic wavelength (2–5 MHz). Velocity vectors 13 describe movement of red blood cells through the sample volume, and the blood flow may be turbulent such that the velocity vectors are oriented in many directions as shown. Also, the red blood cell population of sample volume 11 is constantly changing and it is necessary to get a number of samples of frequency shifted echoes in order to realize an accurate value of velocity. By defocusing the ultrasonic beam to cover the whole area of the vessel lumen, the contribution of many points is averaged out physically to arrive at the value of mean velocity. Averaging is performed over a wide region or area so as to enable calculation of a more accurate value of mean flow velocity. The alternative is to make many determinations of flow velocity at small sample volumes, taking a lot of points which are then averaged, but this procedure is, of course, more time consuming and is not a real time technique.

FIGS. 2 and 3 relate to implementation of the concept that the size of the sample volume is made approximately equal to the diameter of the vessel cross section by programmable aperture synthesis, which electronically tailors the beam spot-width at the required range. The number of active transducer array elements for transmit and receive is varied to realize an ultrasonic beam cross section that is approximately equal to the vessel cross section. Preferably the number of active transducer array elements for transmit and receive are equal. More active elements yield a small beam cross section and fewer active elements yield a wider beam cross section. FIG. 2 shows a portion of a linear array with a relatively small number of active transmit-receive elements 14. The beam profile of a transmitted ultrasonic beam at a scan angle $\theta = 0°$ is indicated at 15; this beam is focused at range R at which the beam spot-width W at the waist of the beam is relatively wide. The active array in FIG. 3 has a larger number of elements 14 and W and the beam cross section at the same range R is considerably smaller. For every scan angle and at various ranges for the scan angle, the beam spot-width W or cross section can be calculated for different numbers of active transmit-receive elements, and this information is stored in a look-up table or read-only memory. Another way to tailor the beam cross section is to use the same number of elements for transmit but vary the number of active elements for receive. The overall sensitivity or discriminating characteristic of the system, as is well known, is the product of transmit and receive functions. The number of transmit elements can remain constant while the number of receive elements is changed, or vice versa, or both may be changed. This in some cases may involve deliberately defocusing the beam. Knowing the scan angle, the range, and the number of transmit and receive elements selected to tailor the beam cross section for blood flow rate measurements, and assuming that the vessel has a circular cross section, the system controller can generate a signal representing estimated vessel cross-sectional area.

The ultrasound imager system is first used to obtain, for example, a longitudinal view of the root of the ascending aorta. This method exploits the anatomical orientation of the aorta which enables one to conveniently image this vessel longitudinally by a transducer array which is positioned in the vicinity of the sub-xyphoid. Abnormal blood flow caused, for instance, by occlusions indicates a heart malfunction or a circulatory system malfunction. Both the ascending aorta and the abdominal aorta are at an intermediate range of about 3–7 cm in the adult. A B-scan display is shown in FIG. 4. A sector-shaped image 16 is built up scan line by scan line on the screen 17 of a cathode ray tube with the system's transducer array positioned to obtain on the display a half-cylinder projection 18 of the vessel. Prior to switching on the Doppler or volume flow rate measurement mode, a beamsteering direction $\theta$ will be selected by the user to coincide with the vessel axis. This will insure that in the Doppler mode of operation, the direction of the ultrasonic beam insonifying the sample volume and the principal flow velocity vector will be colinear. To facilitate system/user interaction in this application, it is desirable to add to the display sub-system the capability of indicating with markers the computed beam width at any range along the Doppler beamsteering direction. The scan angle and range are adjusted electronically by the user with the aid of a visual beamsteering direction and range marker 19. The number of active transducer elements is adjusted with the aid of a beam width marker 20 until the length of the visual marker approximately coincides with the width of the imaged vessel 18. This procedure insures that in the Doppler mode the sample volume interrogated is accurate both in position and size. In practice, the vessel may not be exactly circular and its cross section may change with time, and the beam cross section is more accurately described as being tear drop shaped. The best fit is made that is possible.

Further information on the Doppler mode of operation will be given before proceeding. Echoes backscattered from red blood cells 12, FIG. 1, are frequency shifted by an amount proportional to the frequency of the incident wave and the velocity of blood flow. Movement of red blood cells through sample volume 11 toward the transducer array compresses the wavelengths of the reflected wave, increasing the frequency, and movement of red blood cells away from the transducer array lengthens the wavelength of the reflected wave, decreasing the frequency. The instrument measures only the component of mean velocity in the direction of the transmitted ultrasound beam indicated by beamsteering direction marker 19. The formula relating the Doppler frequency shift and velocity is $$\Delta f = 2 f_o \nu \cos \theta / c) \qquad (1)$$

where $\Delta f$=frequency shift, $f_o$=ultrasound emission frequency, v=mean velocity of blood flow, $\theta$=orientation angle of ultrasonic beam, and c=speed of sound in tissue (1450 m/sec). If the ultrasound beam direction and vessel axis do not coincide, the orientation angle can be measured on the display and a correction made in the computed volume flow rate. The range of blood velocities for humans is known and Doppler shifts are in the audio spectrum of about 0.2 KHz to 8 KHz. As was mentioned, the red blood cell population of sample volume 11 is constantly changing and it is necesary to get a number of samples of frequency shifted echoes in order to calculate an accurate value of velocity. The present duplex system acquires sixteen samples in the Doppler mode for each velocity determination, i.e., there are sixteen ultrasound pulse transmissions and sixteen in-phase and sixteen quadrature focused echo signals are generated and gated to the Doppler processor, but some other number of samples can be acquired. Red blood cells 12 moving past sample Volume 11 backscatter ultrasonic energy containing a spectrum of Doppler frequencies. These correspond to the distribution of velocities present in the sample region and mean velocity can be calculated by averaging the components of the distribution.

The preferred embodiment of the ultrasound system depicted in simplified block diagram form in FIG. 5 is a real time single-sector steered beam scanner into which is incorporated a Doppler and volume flow rate modality. Common linear transducer array 21 is comprised of piezoelectric elements 22 having a greater interelement spacing for receive than for transmit to yield a wide aperture system with low side lobe artifacts using a minimum number of relatively expensive receiver channels. The transmit array is at the center of a larger receive array (elements in the center function dually as transmit and receive elements), and the transmit elements are associated with a pulser 23 capable of generating single impulses for B-scan operation so as to produce wide bandwidth ulstrasound pulses, and multiple impulses for Doppler and volume flow rate operation having a frequency equal to the required emission frequency so as to generate narrow bandwidth ultrasound pulses. The repetition frequency of multiple impulse excitation is variable and has high, intermediate, and low settings selected by a controller 24 with user inputs. Characterization of the transmitted ultrasonic energy as pulses of ultrasound which propagate along a given scan line or as acoustic beams is conventional in the art.

During successive transmission periods of the B-scan mode, pulser 23 generates a series of excitation impulses 25, one per transmit element, with a time delay between successive impulses that is incremented from one transmission period to the next to thereby transmit wide bandwidth pulses of ultrasound along many different scan lines covering the region of a body 26 being examined. A total sector scan angle of approximately 90° is indicated by dashed lines 27. During alternate reception periods, the received echo signals caused by energy echoing from various body structures and detected by receive elements in transducer array 21 are individually amplified and fed to echo processing channels. The receiving channels feature the use of base band signal processing to achieve good lateral resolution while greatly reducing the required time delay accuracy and instead requiring more easily achieveable phase focusing accuracy, and have as major components a receiver 28, a balanced demodulator and low pass filter 29, a time delay device 30 such as a delay line, and a pair of summers 31. These are fully described in U.S. Pat. No. 4,155,260 granted on May 22, 1979 to W. E. Engeler and J. J. Tiemann, the disclosure of which is incorporated herein by reference. In practice, three receiver system parameters are varying during the course of an echo reception period, these being the time delay between elements, the reference signal of the balanced demodulators, and also the receive aperture width. The outermost receiving channels are blanked progressively at shorter ranges to reduce the receive aperture by steps and realize improved lateral resolution near the skin. For B-scan operation, the summed and focused in-phase ($\Sigma I$) and quadrature ($\Sigma Q$) signals are further processed in circuit 32 to derive a resultant signal obtained by squaring the $\Sigma I$ and $\Sigma Q$ components, adding together the squared signals, and taking the square root of the sum. The resultant is the video signal and it is post-processed to improve the image before being fed to cathode ray tube 33 as the Z control or to control the electron beam intensity. Sector-shaped image 16 is built up radial scan line by radial scan line as the transmitted beam direction is changed incrementally, and is a two-dimensional picture of a planar slice through the body which is displayed in real time.

The hand-held ultrasonic probe containing transducer array 21 is acoustically coupled to the skin by a coating of a gel and is adjusted by the user to image a longitudinal view of aorta 18. In the Doppler and volume flow rate orientation mode, a beamsteering direction $\theta$ is selected by the user to coincide with the vessel axis. The sample volume for Doppler interrogation is identified as having coordinates R,$\theta$ along scan line 34. Beamsteering direction and range marker 19 and beam width marker 20 (see FIG. 4) are illuminated on the display screen, and a sample volume is established which spans the vessel diameter. The system's aperture specification facility in controller 24 is ordinarily used to dynamically activate transducer array elements, in order to synthesize an appropriate aperture that is compatible with range and lateral resolution requirements. In this application, however, the aperture specification facility is used such that the number of elements activated will synthesize an acoustic beam whose spot-width at the desired range approximately illuminates the area shown in the display to correspond to the vessel cross section. As the number of active transducer elements for transmit and receive is changed, beam width marker 20 is observed and its length is adjusted to approximately to coincide with the width of the imaged vessel. Knowing R and θ and the beam width W, an area signal representative of the insonified vessel cross section is produced using a look-up table in system controller 24.

In the Doppler and volume flow rate mode of operation, narrow bandwidth pulses of ultrasound are transmitted only along the chosen scan line intersecting the sample volume and range gating is employed to sample echoes from the required depth. The selected transmit elements are repetitively pulsed at a frequency equal to the set emission frequency; this causes the response bandwidth of the transducer to be narrowed. Another feature of the Doppler modality transducer excitation is variable repetition intervals for the multiple excitation in order to be able to adequately sample, at various ranges, backscattered echoes from slow as well as fast moving blood cells. The received echo signals are processed through the quadrature receiving channels and are electronically steered and dynamically focused in exactly the same manner as for B-scan imaging except that only the selected receive elements and associated receiving channels are active and contribute to the focused in-phase and quadrature signals ($\Sigma I$ and $\Sigma Q$). Focused signals are sampled at a specific time after each transducer excitation interval which corresponds to the time taken for the ultrasonic echoes to return to the transducer from range R. A range gate 35 is opened by controller 24 for a relatively short interval at a time corresponding to reception of echoes backscattered from sample volume 11 (FIG. 1) and extracts of a pair of analog samples in parallel. These are fed to a Doppler processor 36 which extracts the spectrum of Doppler shifted components backscattered from the sample volume. This sub-system embodies a complex arithmetic implementation of the Fourier transform and is preferably a real time digital Fast Fourier Transform (FFT) processor. At the output is a multi-point representation of the spectral components corresponding to the velocity distribution in the sample volume. A mean velocity computation circuit 37 such as a weighted summation network, either analog or digital, must be added to the processor to calculate mean velocity.

An estimated vessel cross-sectional area signal is made available by system controller 24. Volume flow rate is then calculated by multiplying the mean velocity reading of the Doppler processor and the area signal. The formula, given previously, is:

$$Q = V \cdot A \quad (2)$$

The multiplication can be performed by the system's computing module or, when a real time output is desired, in a volume flow rate computation circuit 38. A hard copy of the evolution of volume flow rate, Q, with time is printed up by a strip chart recorder 39. FIG. 5 also shows a strip chart recorder 40 for Doppler output information, i.e., bidirectional blood flow velocity versus time.

Figure 6:
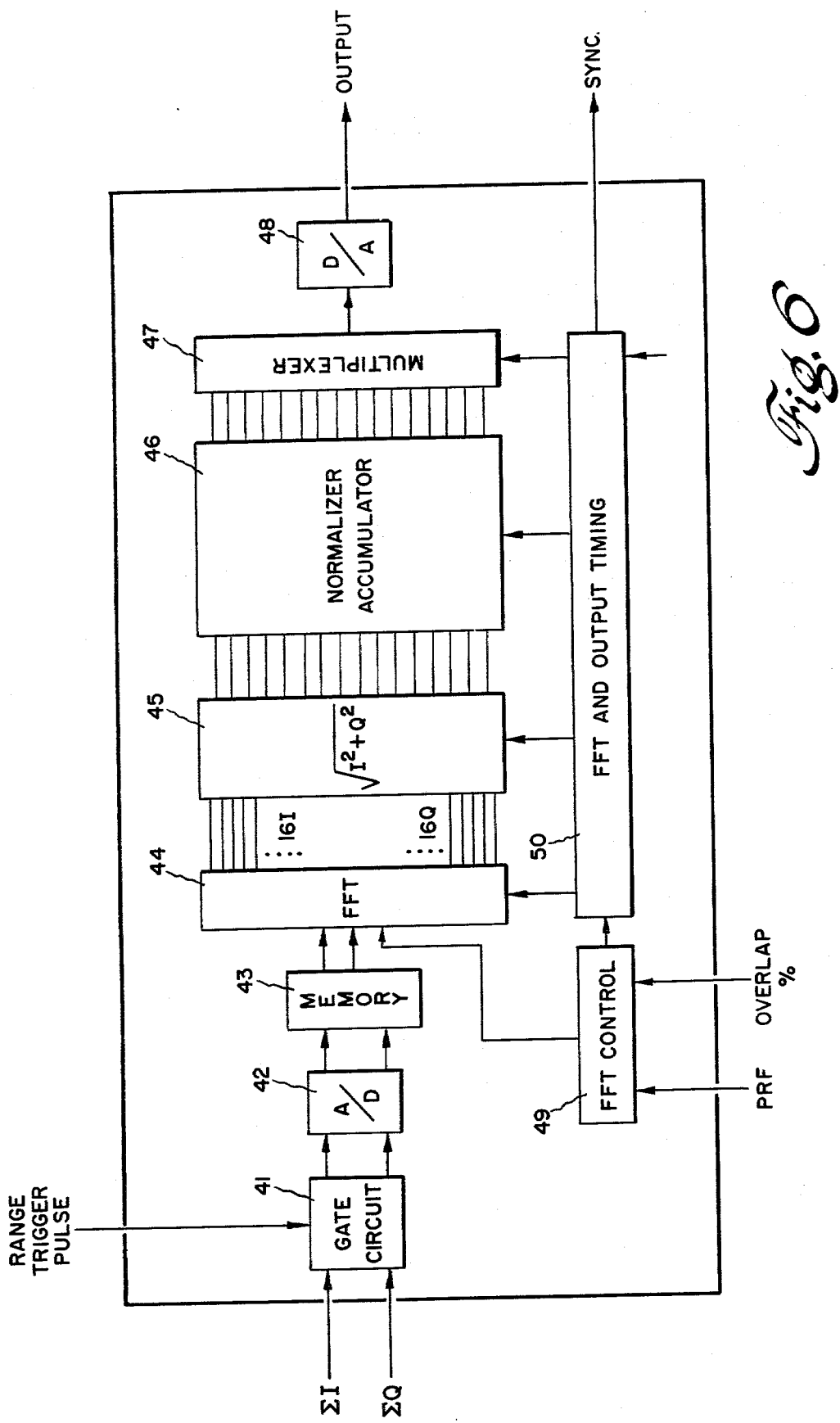
FIG. 6 is a block diagram of the Doppler subsystem.

FIG. 6 is a block diagram of Doppler processor 36 and is fully described in copending application Ser. No. 936,111, filed August 23, 1978, now U.S. Pat. No. 4,217,909, E. Papadofrangakis and W. E. Engeler, "Directional Detection of Blood Velocities in an Ultrasound System,". This sub-system extracts a Doppler frequency spectrum from sixteen focused echo signals, computes the power spectrum, and generates an analog output that represents sixteen Doppler frequencies. Half of these frequencies correspond to positive Doppler shifts (forward flow) and the other half to negative shifts (receding flow). The processor operates in real time with the system running at pulse repetition frequencies of 4 KHz, 8 KHz, and 16 KHz. When processing time is available, particularly at higher pulse repetition frequencies, the processor integrates several spectra before reporting results. The processor can operate on data samples in one of two ways resulting in either a block or a sliding transform.

Gate or sampling circuit 41 corresponds to range gate 35 and has a sampling interval that is very short, such as 0.1 microseconds, as compared with the time duration of the ultrasound pulse to realize velocity measurements with maximum sensitivity at a specific point in the bloodstream. Upon the occurrence of a range trigger pulse, gate circuit 41 passes a pair of analog samples to analog-to-digital converter 42 and the pairs of digitized samples are stored in a memory 43. Doppler processor 44 features a digital implementation of a sixteen-point real time Fast Fourier Transform. The number of transform points is determined by the minimum desirable spectral resolution and a tradeoff of range and velocity discrimination. FFT 44 is constructed with eight CE chips such as are disclosed and claimed in U.S. Pat. No. 4,020,334, N. R. Powell and J. M. Irwin, "Integrated Arithmetic Unit for Computing Some Indexed Products," the disclosure of which is incorporated herein by reference. These CE chips provide complex arithmetic for a sixteen-point digital FFT based on radix 4 algorithm. The digital FFT computation gives an ordered output frequency spectrum comprising sixteen frequency bins, half of which correspond to positive Doppler shifts and the other half to negative shifts. An output spectrum can be calculated once sixteen I and sixteen Q samples from sixteen consecutive echo returns are accumulated in memory 43. These samples are Fourier transformed to produce sixteen real and sixteen imaginary coefficients, and the power spectrum is obtained by squaring and adding the coefficients on a 1:1 basis. Movement of the red blood cells causes rotation of an I-Q phasor in a unit circle. The rate of rotation indicates velocity, direction of rotation gives flow sense. It is a property of the Discrete Fourier Transform (DFT) that contradirected velocities produce complex output numbers corresponding to different velocity bins. In this way, a complex arithmetic Fourier transform permits a separation of the Doppler spectra for forward or receding flow.

The outputs of FFT processor 44 are sixteen I and sixteen Q signals representing frequency shifts, and sixteen resultant signals are generated for display in circuit 45 by squaring corresponding I and Q signals, adding the squares and taking the square root of the sum. The sixteen resultant signals, half for forward flow and half for receding flow, are fed to an accumulator normalizer 46 for presentation to the display either in block transform mode or sliding transform mode. In the first exclusive sets of analog sample pairs are analyzed, i.e., pulse-echo cycles 1-16, 17-32, 33-48, etc. In the latter mode overlapping sets of analog sample pairs are analyzed, i.e., pulse-echo cycles 1-16, 4-20, 8-24, etc. Video output data passes through a multiplexer 47 where it is multiplexed with an ECG signal, and is then fed to a digital-to-analog converter 48 to generate the output data. Input commands for the control units come from controller 24. Block 49 is the FFT control and its inputs are a transform slide number command and a velocity scaling command, and block 50 is FFT and output timing circuitry. At each instant in time, the Doppler processor reports the ultrasound power spectra backscattered from the sample volume, and this corresponds to the velocity distribution in the sample volume. The distribution contains eight positive and eight negative readings.

Figure 7:
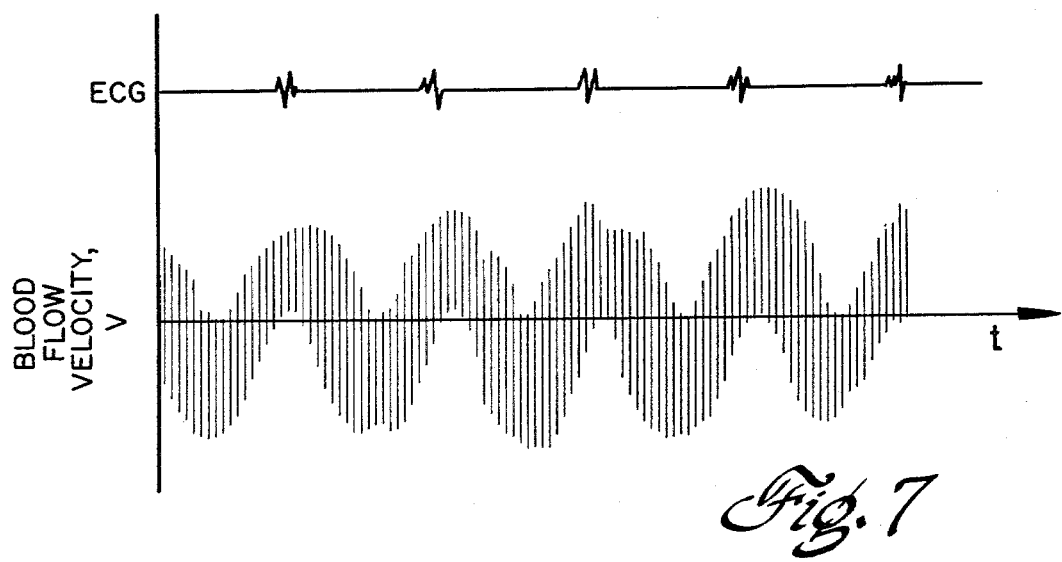
FIG. 7 is a velocity vs. time display for the Doppler mode and of an optional ECG reference.

The entire distribution of blood flow velocities is displayed in FIG. 7 and this approach is preferred in situations of turbulent flow. A plot of bidirectional velocities versus time with a distribution of velocities at every time coordinate is printed by recorder 40. A multiplexed ECG (electrocardiogram) signal provides a heart cycle time reference. The velocity scale of the recorder is coordinated with the selection of pulse repetition frequency that the system is using.

Figure 8:
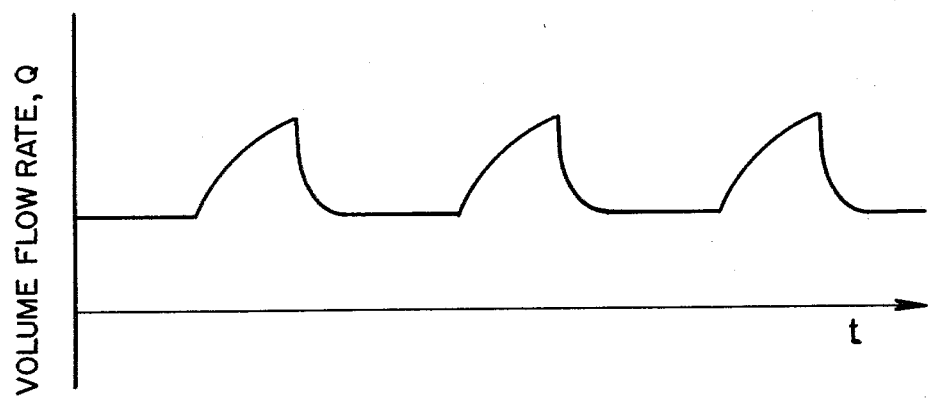
FIG. 8 is a recording of volume flow rate vs. time.

The distribution of velocities computed by Doppler processor 36 are averaged in mean velocity circuit 37 to yield the mean value of the velocity of blood flow over the vessel cross section. More particularly, the first moment of the distribution is calculated. FIG. 8 is a typical print out of volume flow rate versus time. There is a valve at the root of the ascending aorta and the pumping action of the heart is evident.

By tailoring the ultrasonic beam cross section at the required range to cover the whole area of the vessel at the point, the sample volume for Doppler interrogation is shaped and this is used to advantage to result in greater accuracy. Reasonable accuracy in the measured volume flow rate is essential to order to infer diagnostic value. By this method, the contribution of many points is averaged out physically; the averaging is done over a wide region so as to give a more accurate measurement. The improved technique enables physicians to utilize the system in order to quantify volume blood flow in the ascending and abdominal aortas, or in other key areas of interest. All of the foregoing applications and patents which have been referenced to provide additional disclosure of the ultrasound imaging system are assigned to same assignee as this invention.

While the invention has been particularly shown and described with reference to preferred embodiments thereof, it will be understood by those skilled in the art that the foregoing and other changes in form and details may be made therein without departing from the spirit and scope of the invention.

The invention claimed is:

1. A method of measuring the volume flow rate of blood and similar liquids using an ultrasound system which generates ultrasonic beams for performing a sector scan and has a common transducer array for imaging and Doppler modalities, comprising the steps of:
   imaging on a B-scan display a vessel through which the volume flow rate is to be measured, and approximately aligning one ultrasonic beam with the axis of said vessel;
   selecting the number of active array transducer elements for transmit and receive to realize a beam cross section that is approximately equal to the vessel cross section at a given range, which is the sample volume, and producing an area signal representative of the latter cross section;
   alternately transmitting ultrasonic beams to insonify the sample volume and detecting received echoes using only the selected active array elements, and processing the received echoes to yield focused in-phase and quadrature signals;
   gating said focused signals after every transmission for a short interval to extract a pair of analog samples representing echoes backscattered from the sample volume;
   analyzing sets of pairs of analog samples to derive the magnitude and sign of the distribution of frequency shifts of echoes with respect to a known ultrasound emission frequency;
   deriving mean flow velocity from said distribution of frequency shifts and generating a signal indicative thereof; and
   presenting said area and mean flow velocity signals to circuitry in which the volume flow rate is calculated.

2. The method of claim 1 wherein said sets of pairs of analog samples are analyzed with a Doppler processor embodying a complex arithmetic implementation of the Fourier transform.

3. The method of claim 2 wherein the volume flow rate is calculated in real time.

4. The method of claim 3 further including the step of visually displaying volume flow rate as a function of time on a strip chart recorder.

5. The method of claim 2 wherein a beamsteering direction and range marker is produced on said B-scan display which is approximately aligned with the axis of the imaged vessel, and wherein a beam width marker is produced whose length is adjusted as the number of active array elements is changed to approximately coincide with the width of the imaged vessel.

6. The method of claim 5 wherein the number of active array elements selected for transmit and receive are equal.

* * * * *